United States Patent [19]

Ford, Jr.

[11] 4,204,330
[45] May 27, 1980

[54] METHOD AND APPARATUS FOR EXTRACTING TEETH

[76] Inventor: James P. Ford, Jr., 101 Canary La., Grand Junction, Colo. 81501

[21] Appl. No.: 900,750

[22] Filed: Apr. 27, 1978

[51] Int. Cl.² ............ A61C 3/10; A61C 3/14; B25B 15/00

[52] U.S. Cl. ............ 433/148; 145/50 A; 433/215

[58] Field of Search ........... 32/61, 64, 40 R, 43, 32/44, 45; 254/131; 29/267; 145/50 A

[56] References Cited

U.S. PATENT DOCUMENTS

| | | | |
|---|---|---|---|
| 1,538,195 | 5/1925 | Levedahl | 145/50 A |
| 2,002,245 | 5/1935 | McDaniel | 32/61 |
| 2,366,671 | 1/1945 | Montelius | 32/61 |
| 2,674,799 | 4/1954 | Fraser | 32/61 |
| 3,060,582 | 10/1962 | Kopp | 32/61 |
| 4,037,514 | 7/1977 | Lliteras | 145/50 A |

*Primary Examiner*—Louis G. Mancene
*Assistant Examiner*—Michael J. Foycik
*Attorney, Agent, or Firm*—Edwin L. Spangler, Jr.

[57] ABSTRACT

This invention relates to an improved tooth elevator characterized by a bit terminating in a blade having a generally S-shaped or reverse S-shaped cross section. The invention also encompasses the novel method of extracting at least one of a pair of adjacent teeth with an elevator having an S-shaped or reverse S-shaped tip which consists of inserting the bit with its axis essentially horizontal in between the teeth to be extracted and rotating said bit about its axis in a direction such that a remote sharpened edge of the S-curve engages one of said teeth at a point spaced from the gum line defining a fulcrum about which the adjacent sharpened edge of the S-curve pivots into prying engagement with the other tooth of the pair nearer said gumline so as to lift the latter out of its socket.

6 Claims, 7 Drawing Figures

METHOD AND APPARATUS FOR EXTRACTING TEETH

Dental elevators for use in extracting teeth are quite old in the art, the bits or endpieces employed in the actual prying of the tooth from the patient's jaw taking many different shapes and forms. Examples of such elevators available commercially can be found on pages 86–88 of the 1977 Darby Dental Supply Co. catalog, this same company's 1976 catalog on pages 6–12, and the following U.S. pat. Nos.:
- Crosthwaite, 273,821
- Crawford, 827,507
- Barry, 1,606,686
- Machat, 2,172,478
- Montelius, 2,366,671
- Fraser, 2,674,799
- Kopp, 3,060,582

To applicant's knowledge, none of the prior art elevators has a generally S-shaped or reverse S-shaped cross section with oppositely-facing sharpened side margins capable of being used in accordance with the unique method of the instant invention wherein the bit is inserted between a pair of teeth to be extracted and then rotated about the bit axis to simultaneously pry both teeth out while tilting them away from one another using one of the sharpened edges as a fulcrum around which the other swings.

It is, therefore, the principal object of the present invention to provide a novel and improved dental elevator.

A second objective is the provision of a unique method of using a dental elevator with a bit having an S-shaped or reverse S-shaped cross section between a pair of adjacent teeth using one of the pair as a fulcrum to lift the other.

Another object of the invention herein disclosed and claimed is to provide a uniquely shaped dental elevator bit that is specially designed for use in a twisting motion between a pair of adjacent teeth.

Still another objective of the herein described invention is the provision of a tooth extraction method and tool for use in accordance therewith which results in less trauma and soft tissue damage many of the prior art tools and methods heretofore employed.

An additional object of the invention forming the subject matter hereof is to provide an elevator of the type aforementioned which come in clockwise and counterclockwise versions, each to be rotated in the direction such that their concave surfaces lead while the convex surfaces thereof trail.

Further objects are to provide a dental elevator which is simple, easy to use, dependable, versatile, safe, relatively inexpensive and even somewhat decorative.

Other objects will be in part apparent and in part pointed out specifically hereinafter in connection with the description of the drawings that follows, and in which.

Figure 1:
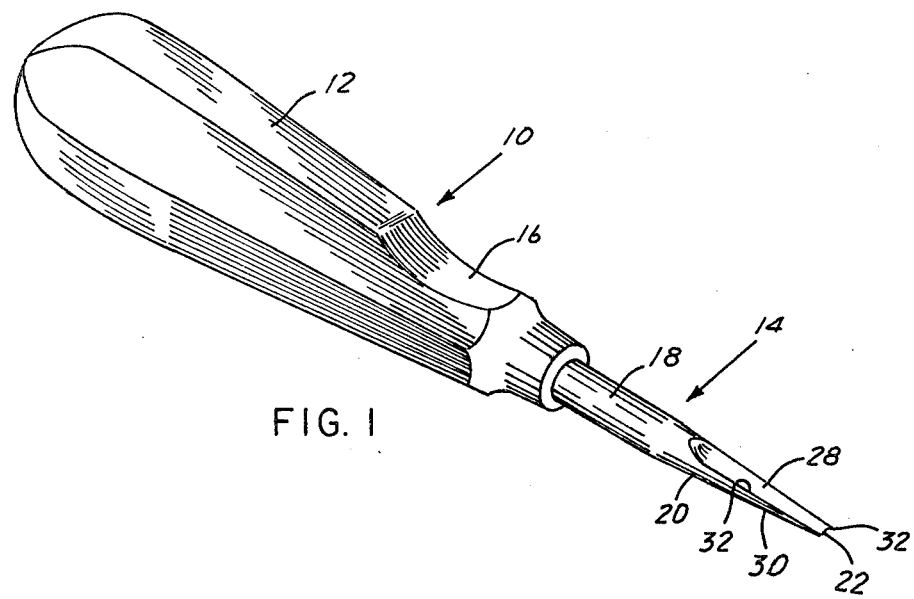
FIG. 1 is a perspective view of the dental elevator of the present invention.
Figure 2:
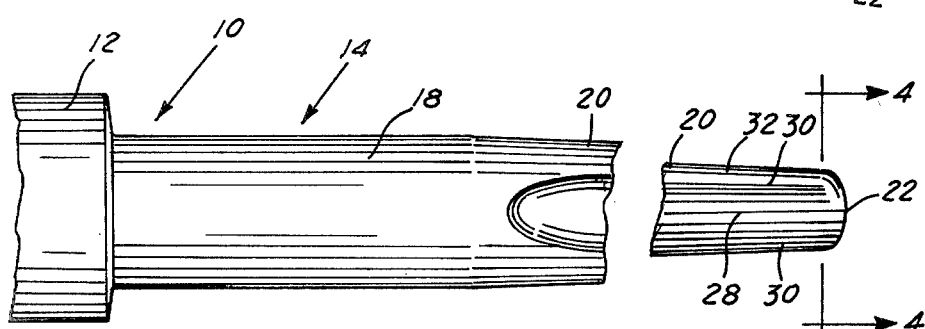
FIG. 2 is a fragmentary plan view to a greatly enlarged scale, portions of which have been broken away to conserve space, showing the bit alone.
Figure 3:
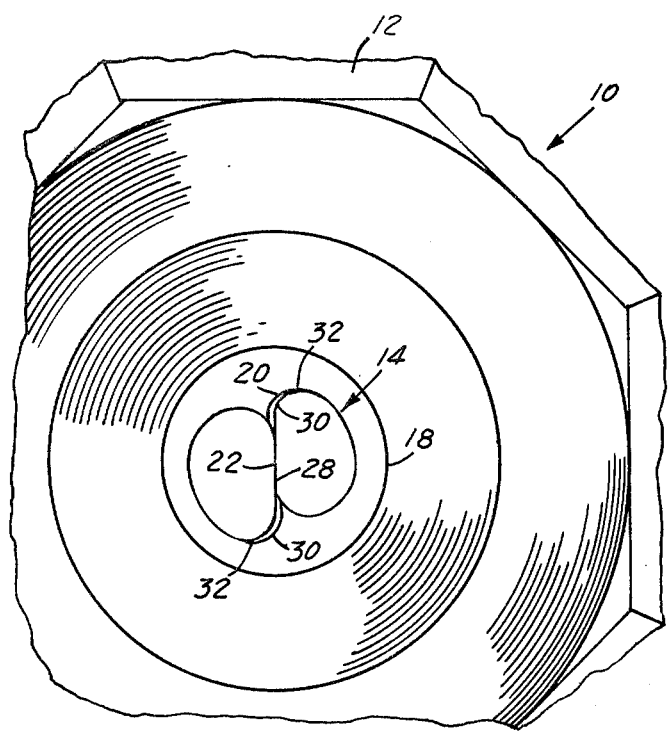
FIG. 3 is a fragmentary end view to a still further enlarged scale showing the tool as seen from the bit end.

Referring next to the drawings for a detailed description of the present invention and, initially, to FIGS. 1–5 for this purpose, reference numeral 10 has been chosen to identify the dental elevator in its entirety while numeral 12 designates its handle and numeral 14 broadly designates the bit thereof. Handle 12 is of conventional design, the particular one shown having a forwardly tapered generally-octagonal cross section with a concave depression 16 for the user's thumb on one of its facets. The particular handle shown is aligned coaxially with the bit 14 and this is preferred although the handle could, without the exercise of invention, be placed transversely of the bit to produce a generally T-shaped tool in the manner of several of the prior art elevators if such were deemed advisable. Accordingly, no novelty whatsoever is predicated upon the handle design, its function being none other than to provide a means for imparting a substantial twisting movement to the bit generally about the longitudinal axis of the latter.

The bit 14 is, in accordance with the general practice followed in the fabrication of such tools, made from hardened tool steel capable of being sharpened to an edge which will dig into and grip the tooth enamel. The particular bit shown has a generally cylindrical shank portion 18 fastened into the handle and a forwardly tapered blade 20 terminating in a rounded end 22. While the taper is not absolutely essential, it is highly desirable in that it allows for adjustment of the blade to fit into different sized gaps 24 between adjacent teeth 26, both of the latter having been shown in FIGS. 6 and 7 to which detailed reference will be made presently.

Figure 7:
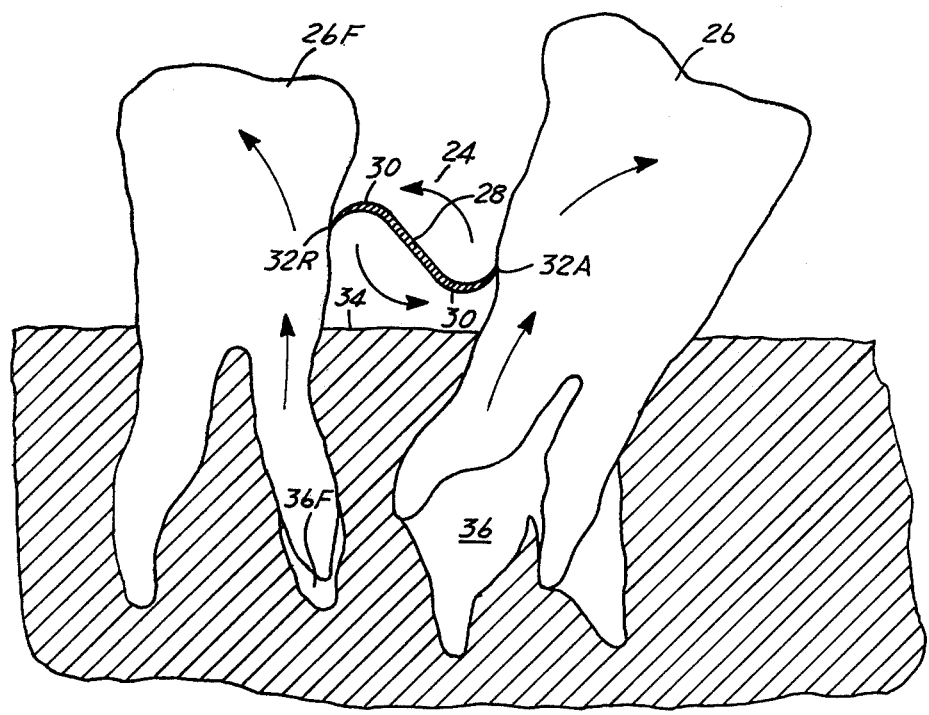

The bit 14 is elongate and straight with no bends or curves therein although, here again, this is not essential provided that its blade 20 can be twisted in the manner of FIG. 7 about it longitudinal axis between a pair of adjacent teeth. There seems, however, to be no real advantage in making the bit other than straight and generally coaxially-aligned with the handle as shown.

Figure 4:
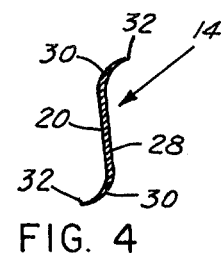
FIG. 4 is a section taken along line 4—4 of FIG. 2 to approximately the same scale as FIG. 3.
Figure 5:
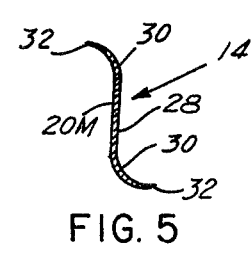
FIG. 5 is a section like FIG. 4 and to the same scale but differing therefrom in that it shows the oppositely-curved bit, the bit of FIG. 4 being used on the tool designed for clockwise rotation while that of FIG. 5 is designed for counterclockwise rotation.

The entire novelty in the tool lies in the cross section of the blade of the bit 14 which is most clearly revealed in FIGS. 4 and 5 to which detailed reference will now be made. This blade 20 has a more or less straight medial section 28 bordered on both sides by oppositely-curved side sections 30 each of which terminates in a sharpened edge 32, the overall result of which is to define a generally S-shaped (FIG. 4) or reverse S-shaped (FIG. 5) cross section. The version of the tool shown in FIGS. 1–4 is designed for counterclockwise rotation by the user while that of FIG. 5 having the oppositely-curved tip 20M is designed for clockwise rotation.

Figure 6:
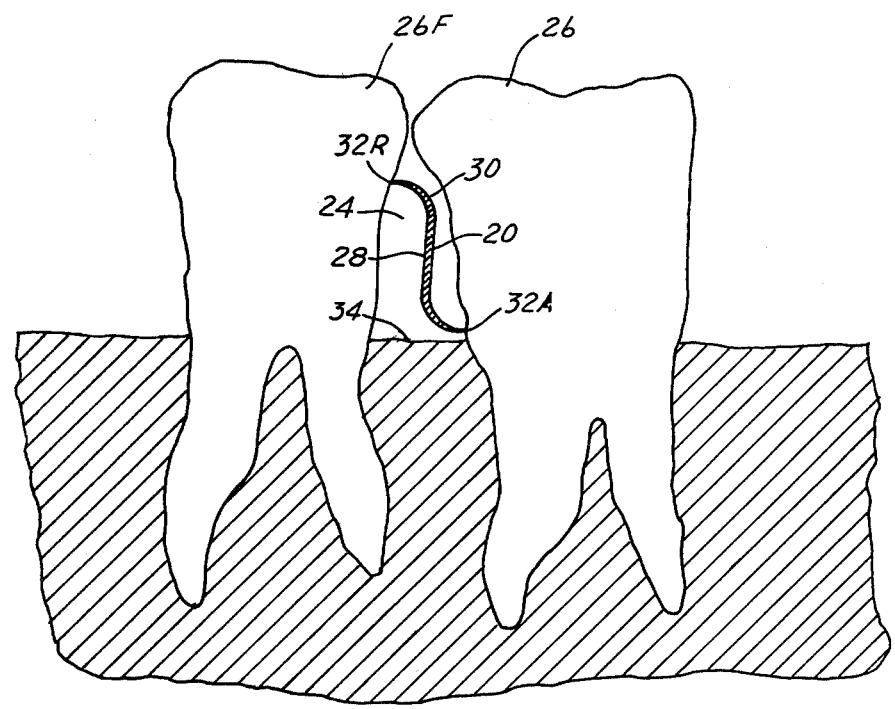
FIG. 6 is a diagram showing the placement of the bit between a pair of adjacent teeth preparatory to being rotated; and, FIG. 7 is a diagram similar to FIG. 6 and to the same scale showing the results of having twisted the tool through approximately a quarter turn.

While on the subject of the direction of tool rotation, it is an appropriate place to shift the attention to FIGS. 6 and 7 where it will be seen that one of the pair of adjacent teeth 26 has been designated the fulcrum tooth 26F, it being the one on the left as shown. Assuming that the dentist is inserting the elevator into the gap 24 from the position occupied by the viewer and that tooth 26F is to be used as the fulcrum tooth, then the tool with blade 20 (FIGS. 1-4) would be used and twisted counterclockwise as indicated in FIG. 7. If, on the other hand, the right-hand tooth of the pair were to be used as the fulcrum, then the tool with reverse/curved blade 20M of FIG. 5 would be used and twisted clockwise. Whichever tool is used, the direction of rotation is always such that the concave surfaces of the side sections 30 lead while the convex surfaces thereof trail. Finally, continuing with FIGS. 6 and 7, the method of using the elevator 10 will next be set forth in detail. Having selected the pivot or fulcrum tooth 26F, the dentist will then select the clockwise or counterclockwise version of the elevator depending upon which is applicable. The bit will next be inserted into the gap 24 between the two teeth with the blade thereof essentially perpendicular. The depth of insertion will depend upon the width of gap 24, the operative position being that in which the remote sharpened edge 32R of the blade engages the fulcrum tooth 26F at a point spaced above the gumline 34, whereas, the adjacent sharpened edge 32A lies at or near the latter. Obviously, the relative vertical positions of edges 32R and 32A will be reversed when extracting teeth from the upper jaw; however, their positions with respect to the gumline will remain the same.

Once the tool is positioned or shown in FIG. 6, the dentist twists it counterclockwise as shown using the pivot tooth 26F and the remote edge 32R engaging same as a fulcrum about which to swing adjacent edge 32A thus prying tooth 26 upwardly and to the right as shown out of its socket 36. The twisting force exerted will be such that some movement of the fulcrum tooth 26F will occur although to a much lesser extent than tooth 26. In many instances, tooth 26F is also to be extracted but, if not, it will reseat in its socket 36F and be none the worse for its role as a fulcrum for the removal of its companion.

What is claimed is:

1. In a dental elevator, the improved bit which comprises an elongate rigid member terminating in a blade of a thickness sized for insertion into the gap between a pair of teeth in side-by-side relation, said blade having a width in excess of the width of said gap and a generally S-shaped or reverse S-shaped cross section defined by a medial portion bordered on both sides by oppositely-curved marginal portions terminating in knife edges, one of said edges upon being placed against the adjacent tooth of a side-by-side pair thereof at a point above the gumline cooperating therewith to define a fulcrum about which the other of said edges can be swung into prying contact with the other tooth of said pair upon rotation of said bit in a direction to lift the latter from its socket.

2. The dental elevator as set forth in claim 1 wherein the blade terminates in a rounded tip.

3. The dental elevator as set forth in claim 1 wherein the side margins of the blade converge in the direction of the free end thereof to accommodate gaps of varying widths.

4. The dental elevator as set forth in claim 1 wherein the marginal portions are curved such that the sharpened edges thereof lie at approximately right angles to the medial portion.

5. The method of prying one tooth of a side-by-side pair thereof from its socket with a dental elevator having a bit terminating in a blade with a generally S-shaped or reverse S-shaped cross section defined by a medial portion bordered on both sides by oppositely-curved marginal portions that terminate in sharpened edges which comprises the steps of inserting the blade between the pair of teeth, placing the sharpened edge of the blade remote from the gumline against the adjacent tooth of the pair, then swinging the sharpened edge adjacent the gumline into contact with the other tooth of said pair, and continuing to rotate the blade in the same direction about said remote edge as a fulcrum to pry said other tooth from its socket.

6. The method as set forth in claim 5 wherein the sharpened edges of the blade converge toward the tip thereof, and wherein the blade is inserted between the pair of teeth to a depth where the gap therebetween is less than the width of the blade measured between the points of contact with the teeth.

* * * * *